United States Patent [19]

Gayral

[11] 4,259,442
[45] Mar. 31, 1981

[54] PROCESS OF RAPID IDENTIFICATION OF BACTERIA OF THE GENUS STREPTOCOCCUS

[75] Inventor: Jean-Pierre Gayral, Lagnieu, France

[73] Assignee: Laboratoire de Recherche Api S.A.R.L., Isere, France

[21] Appl. No.: 945,910

[22] Filed: Sep. 26, 1978

[30] Foreign Application Priority Data

Oct. 4, 1977 [FR] France .................... 77 30613

[51] Int. Cl.³ .............................................. C12Q 1/14
[52] U.S. Cl. ........................................ 435/36; 435/14; 435/253; 435/882
[58] Field of Search ....................... 135/36, 253, 4, 25, 135/26, 18, 14, 882; 422/56, 57

[56] References Cited

U.S. PATENT DOCUMENTS

| 3,616,251 | 10/1971 | Linoli .................... 435/18 X |
| 3,699,003 | 10/1972 | Kronish et al. .......... 435/36 |
| 3,790,447 | 2/1974 | Hirata et al. ............ 435/36 X |

OTHER PUBLICATIONS

J. L. Maddocks & Mary Jo Greenan, A Rapid Method For Identifying Bacterial Enzymes; Journal of Clinical Pathology, vol. 28, No. 8, 1975, pp. 686–687.

Hans-Ulrich Bergmeyer, Methods of Enzymatic Analysis, pp. 151–155, 419–422, 460, 461, 783–785; 1965.

Chemical Abstracts, vol. 67, 951u; 1967.

Chemical Abstracts, vol. 75, 30361j; 1971.

*Primary Examiner*—Robert J. Warden
*Attorney, Agent, or Firm*—Browdy and Neimark

[57] ABSTRACT

Rapid identification of different species of Streptococcus is accomplished by: culturing the bacteria for several hours under unusual conditions which induces the bacteria to create characteristic enzymes by which the bacteria can be identified, and in a medium containing no more than about 1 g of glucose per liter of culture medium to produce a dense culture; distributing the culture onto several supports containing different substrates which are capable of reacting with enzymes so produced by different species of Streptococcus under the unusual conditions; and incubating the culture to produce a distinctly colored or colorable reaction product.

13 Claims, No Drawings

4,259,442

PROCESS OF RAPID IDENTIFICATION OF BACTERIA OF THE GENUS STREPTOCOCCUS

FIELD OF INVENTION

The present invention relates to a process of rapid identification of bacteria of the genus Streptococcus.

BACKGROUND OF INVENTION

In bacteria belonging to the genus Streptococcus are found species that are very different in their bacteriological criteria. Thus, the methods of identification now in use make it possible using serological techniques, to classify Streptococci into different serogroups designated by the letters A to H and K to T, the groups have been found to be responsible for infections in man or animal being, in order of importance, the following: A, D, B, C, G, H, F and K.

There also exist methods of identification of these bacteria based on their nutritional characteristics. In these methods, two series of tests are applied:

Determination of the growing capacity of the bacteria in "hostile" media, the bacteria being inoculated in one or more culture media whose physical and chemical characteristics are made unusual, either by addition of inhibitors, by keeping the pH conditions very basic or by keeping the incubation temperatures abnormally low or high.

Determination of the ability to use natural carbon substrates in a complete culture medium: assimilation of simple sugars.

These identification methods have always had the drawback of requiring long implementation, which can exceed 48 hours, and their empirical nature makes them inexact.

SUMMARY OF INVENTION

The present invention is intended to make possible the rapid identification of bacteria of the genus Streptococcus. Thus, it relates to a process of rapid identification of bacteria of the genus Streptococcus characterized by a colorimetric display of characteristic enzymes of these bacteria after culture of such bacteria in a medium stimulating production of these enzymes.

DETAILED DESCRIPTION OF EMBODIMENTS

Actually it is known that bacteria have a constitutive enzymatic capacity, i.e. they are capable of performing a certain number of reactions necessary for their growth.

But bacteria can also have an inducible enzymatic capacity; this means that in the absence of the usual nutrients or in the presence of an insufficient amount of these nutrients (such as glucose) and in the presence of unusual nutrients (such as a $\beta$-glucoside), the bacterium can manufacture the enzyme or enzymes (here $\beta$-glucosidase) necessary for conversion, e.g. by degradation, of the unusual nutrient into the usual nutrient. In the present case, $\beta$-glucoside is transformed into glucose under the action of $\beta$-glucosidase. This usual nutrient then participates in the development of the bacterium by means of the constitutive enzymes.

Finally, the bacteria can have their inducible enzymatic capacity repressed; this means that in case the bacterium is simultaneously in the presence of sufficient amounts of usual and unusual nutrients, manufacture of the enzyme or enzymes necessary for degradation of the unusual nutrient is prevented or repressed by the presence of the usual nutrient.

Systematic study of numerous classes of substrates, i.e. compounds capable of reaction with induced enzymes, has now made it possible to select certain families of such substrates, known per se, for use to identify the bacteria colorimetrically by reaction with the induced enzymes. These enzymes have never been applied to identification of Streptococci or have been used in too partial a manner to make it possible to detect their discriminating advantage.

According to a first characteristic of the invention, Streptococci belonging to groups A and D can be induced to produce an enzyme of the arylamidase class which can be characterized by hydrolysis of the molecule of pyrrolydonyl-$\beta$-naphthylamide or the corresponding nitroanilide, namely pyrrolydonyl nitroanilide.

Streptococci belonging to groups C and G can be induced to produce an enzyme of the osidase class and more precisely of the glycuronidase type which will advantageously be characterized by hydrolysis of naphthol ASBI $\beta$ D glucuronic acid or of the corresponding methylumbelliferyl derivative, namely methylumbelliferyl $\beta$ D glucuronic acid.

Streptococci belonging to group D can be induced to produce two different enzymes, both of the osidase class. According to the invention, the enzyme of Streptococci belonging to group D, which is of the glucosaminidase type, is characterized by hydrolysis of naphthyl-N-acetyl $\beta$ D glucosamine or the corresponding nitrophenyl or methylumbelliferyl derivative, such as nitrophenyl-N-acetyl-$\beta$-D glycosamine or methylumbelliferyl-N-acetyl-$\beta$-D glucosamine.

The enzyme of Streptococci of group D, whic is the $\beta$ glucosidase type, is advantageously characterized by hydrolysis of 6-bromo-2-naphthyl-$\beta$-D glucopyranoside or the corresponding nitrophenyl or methylumbelliferyl derivative, such as nitrophenyl $\beta$-D-glucopyranoside or methylumbelliferyl $\beta$-D glucopyranoside.

Streptococci belonging to groups A, B, C and G can be induced to produce an enzyme of the phosphatase class and which, according to the invention, is characterized by hydrolysis of 2-naphthyl phosphate or the corresponding nitrophenyl derivative, such as nitrophenyl phosphate.

In the process of rapid identification of bacteria of the genus Streptococcus according to the invention, display of the above enzymes, taken together or separately, is performed after putting a substrate into contact with a bacterial culture of Streptococci made in a medium, the composition of which induces the making, by the bacteria, of certain characteristic enzymes as noted above. The influence of this culture medium is therefore determining because the response of a given substrate, in the presence of the same bacterium, will be different depending on the medium on which this bacterium is grown.

Applicant has found that production of the characteristic enzymes of bacteria of the genus Streptococcus, according to the invention, is optimal when the glucose content of the culture medium is less than or equal to 1 g per liter. A typical composition for the culture medium is given below:

| | |
|---|---|
| Casein trypsin peptone | 8.2 g |

-continued

| | |
|---|---|
| Soya papain peptone | 1.0 g |
| Sodium chloride | 1.7 g |
| Monopotassium phosphate | 0.83 g |
| Meat peptic peptone | 2.5 g |
| Yeast extract | 5.0 g |
| Tris(hydroxymethyl) aminomethane | 3.0 g |
| Hemin | 0.01 g |
| Cystine | 0.4 g |
| Glucose | 1.0 g |
| Distilled water (enough for) | 1000 ml |
| the pH being kept at 7.6 ± 0.2. | |

Practice of the process according to the invention is advantageously performed on a support described in French Pat. No. 76 05 165 (copending U.S. application Ser. No. 769,277). This support is made up of a certain number of disks prepared from a layer of fibers that are chemically inert and insoluble in current organic solvents, these fibers having a loose and sufficiently fine texture to permit adsorption and uniform distribution of the reagents over their entire surface, the layer being impregnated with an alcohol solution of a substrate and a pH stabilizer which is highly soluble in water.

The disks are placed on the bottom of a corresponding number of cupules or cavities in a plate made from a material that is inalterable under test conditions. The process of rapid identification of bacteria according to the invention comprises cultivating the bacterium to be identified in the culture medium of the composition mentioned above, or a similar composition, so that the bacterium is induced to manufacture the characteristic induced enzymes until a dense culture is obtained (5 to 24 hours).

The culture is then distributed in a certain number of cupules containing the supporting disks impregnated with various reactive substrates.

The so distributed cultures with the various substrates are allowed to incubate for 2 to 5 hours at a temperature on the order of 37° C., after which there is deposited on each of the supports a reagent which gives a colored product of reaction with the enzymatic degradation product or products of the substrate, in case the degradation product of the substrate is not itself colored. The colors observed are then used to classify the bacterium as one of the Streptococcus groups (A/pyogenes, B/agalactiae, C, D, G, etc. . . .).

Thus, for example, under the action of a β-glucosidase made by the bacteria, the substrate 6-bromo-2-naphthyl β-D-glucopyranoside is split into 6-bromo-2-naphthol and glucopyranoside, colorless compounds; addition of a diazonium salt, such as past blue BB gives a violet coloring by coupling with the naphthol.

Also, under the action of a glycylglycylaryl-amidase, the substrate glycylglycyl-β-naphthylamide is split into glycylglycine and 2-naphthylamine, the coupling of this latter compound with the diazonium salt mentioned above leading to the formation of an orange coloration.

Under the action of a phosphatase, the substrate 2-naphthylphosphate is split into phosphoric acid and 2-naphthol, whose coupling with past blue BB gives a violet coloration.

It is understood that these few examples of colorimetric reaction have been given only by way of indication and in no way limit the scope of the invention.

What is claimed is:

1. A process for the rapid identification of bacteria of the genus Streptococcus, comprising:

culturing an unknown Streptococcus bacteria in a culture medium containing glucose in an amount sufficient to stimulate the production of an enzyme characteristic of Streptococci bacteria and said enzyme being selected from the group consisting of pyrrolydonyl arylamidase, β-glucuronidase, β-glucosidase, N-acetyl-β-glucosaminidase and phosphatase, and thereby stimulating the production of said enzyme by said unknown bacteria;

mixing the so cultured unknown bacteria containing said enzyme with a substrate capable of reacting with said enzyme to produce a distinctly colored product or a product easily convertible to a distinctly colored product by reaction with a reagent; and incubating the culture with the substrate to obtain the product whereby the bacteria is identified by colorimetric display.

2. Process according to claim 1, wherein the medium stimulating the production of the characteristic enzyme contains at a maximum 1 gram glucose per liter of medium.

3. Process according to claim 1 or 2, wherein the identification of Streptococci A and D is effected by the showing of pyrrolydonyl arylamidase, by hydrolytic splitting of pyrrolydonyl β naphthylamide or pyrrolydonylnitroanilide.

4. Process according to claim 1 or 2, wherein the identification of Streptococci C and G is effected by showing of B glucuronidase, by hydrolytic splitting of naphthol β D glucuronic acid or methylumbelliferyl β D glucuronic acid.

5. Process according to claim 1 or 2, wherein the identification of Streptococcus D is effected by the showing of N-acetyl-β glucosamidinase, by hydrolytic splitting of naphthyl N acetyl β D glucosamine or the corresponding nitrophenyl or methyl umbelliferyl derivatives, such as nitrophenyl-N-acetyl-β-D-glucosamine or methyl umbelliferyl-N-acetyl-β-D-glucosamine.

6. Process according to claim 1 or 2, wherein the identification of Streptococcus D is effected by the showing of β glucosidase, by hydrolytic splitting of 6-bromo-2-naphthyl-β-D-glucopyranoside or the corresponding nitro-phenyl or methyl umbelliferyl derivatives, such as nitrophenyl-β-D-glucopyranoside or methyl umbelliferyl-β-D-glucopyranoside.

7. Process according to claim 1 or 2, wherein identification of Streptococci A, B, C and G is effected by the showing of phosphatase, by hydrolytic splitting of 2-naphthylphosphate or nitro-phenylphosphate.

8. Process according to claim 1 or 2 wherein said culturing is carried out for 5–24 hours, and said incubating is carried out for 2–5 hours at about 37° C.

9. Process according to claim 8 wherein said substrate is supported on a fibrous support of a layer of inert and insoluble fibers, and said fibrous support is impregnated with an alcohol solution of said substrate and a pH stabilizer.

10. Process according to claim 9 wherein the pH of said culture medium is 7.6±0.2.

11. Process according to claim 10 wherein said culture medium has the following approximate composition:

| | |
|---|---|
| Casein trypsin peptone | 8.2 g |
| Soya papain peptone | 1.0 g |

-continued

| | |
|---|---|
| Sodium chloride | 1.7 g |
| Monopotassium phosphate | 0.83 g |
| Meat peptic peptone | 2.5 g |
| Yeast extract | 5.0 g |
| Tris(hydroxymethyl) aminomethane | 3.0 g |
| Hemin | 0.01 g |
| Cystine | 0.4 g |
| Glucose | 1.0 g |
| Distilled water (enough for) | 1000 ml |

12. Process according to claim 1 wherein said incubating is carried out by putting said culture of bacteria into contact with several substrates, each said substrate being specific to one of said enzymes.

13. A device for carrying out the process of claim 12 comprising a series of fibrous supports, a first said support being impregnated with a substrate capable of reacting with pyrrolydonyl arylamidase to produce a distinctly colored product or a product easily convertible to a distinctly colored product by reaction with a reagent; a second said fibrous support being impregnated with a substrate capable of reacting with $\beta$-glucuronidase to produce a distinctly colored product or a product easily convertible to a distinctly colored product by reaction with a reagent; a third said fibrous support being impregnated with a substrate capable of reacting with N-acetyl-$\beta$-glucosaminidase to produce a distinctly colored product or a product easily convertible to a distinctly colored product by reaction with a reagent; a fourth said fibrous support being impregnated with a substrate capable of reacting with $\beta$-glucosidase to produce a distinctly colored product or a product easily convertible to a distinctly colored product by reaction with a reagent; and a fifth said fibrous support being impregnated with a substrate capable of reacting with phosphatase to produce a distinctly colored product or a product easily convertible to a distinctly colored product by reaction with a reagent.

* * * * *